(12) United States Patent  (10) Patent No.: US 6,416,464 B2
Elliott  (45) Date of Patent: Jul. 9, 2002

(54) KIT FOR ENHANCED USE OF AN OTOSCOPE

(76) Inventor: Peter Christopher Elliott, 3304 Santee, Austin, TX (US) 78733

( * ) Notice: Subject to any disclaimer, the term of this patent is extended or adjusted under 35 U.S.C. 154(b) by 0 days.

(21) Appl. No.: 09/923,308

(22) Filed: Sep. 28, 2001

Related U.S. Application Data

(63) Continuation-in-part of application No. 09/517,119, filed on Mar. 7, 2000, which is a continuation-in-part of application No. 09/398,287, filed on Sep. 20, 1999, now Pat. No. 6,165,125, which is a continuation-in-part of application No. 09/306,210, filed on May 6, 1999, now Pat. No. 6,001,059, which is a continuation-in-part of application No. 09/080,894, filed on May 18, 1998, now Pat. No. 5,938,590.

(51) Int. Cl.[7] ............................................. A61B 1/227
(52) U.S. Cl. ........................................ 600/184; 600/200
(58) Field of Search ................................ 600/184, 200, 600/199; 606/106, 162

(56) References Cited

U.S. PATENT DOCUMENTS

| 5,390,663 | A | * | 2/1995 | Schaefer | 600/200 |
| 5,938,590 | A | * | 8/1999 | Elliott | 600/200 X |
| 6,001,059 | A | * | 12/1999 | Elliott | 600/200 X |
| 6,165,125 | A | * | 12/2000 | Elliott | 600/200 |

FOREIGN PATENT DOCUMENTS

| FR | 2566668 A1 | * | 1/1986 | 600/200 |
| GB | 1026208 A | * | 4/1966 | 600/200 |
| GB | 2185688 A | * | 7/1987 | 600/200 |

* cited by examiner

*Primary Examiner*—Jeffrey A. Smith
(74) *Attorney, Agent, or Firm*—Joseph F. Long

(57) ABSTRACT

Differing shaped fittings to retrofit an otoscope to use to inspect and remove foreign material from a nose or an ear depending upon need and fittings to allow use of foot pressure or finger pressure to vary internal pressure in the otoscope are provided within kits of differing makeups.

10 Claims, 5 Drawing Sheets

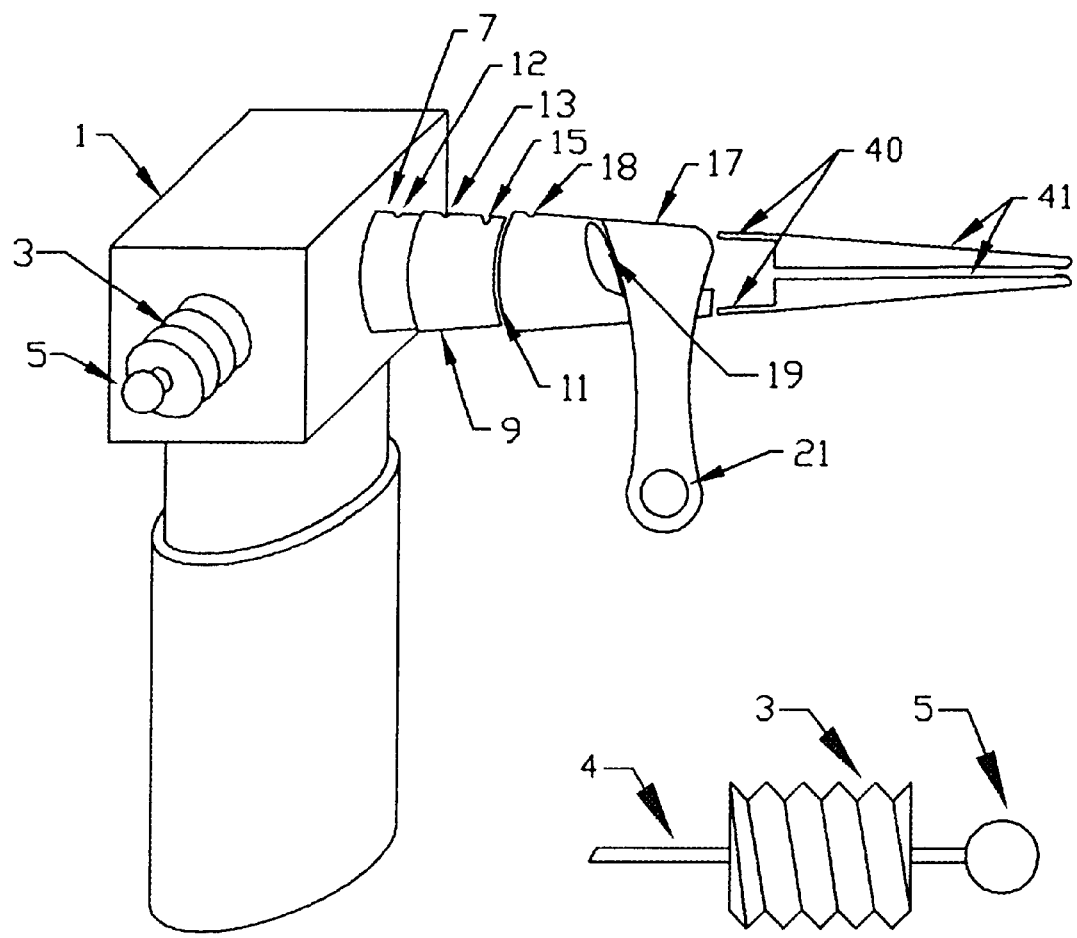
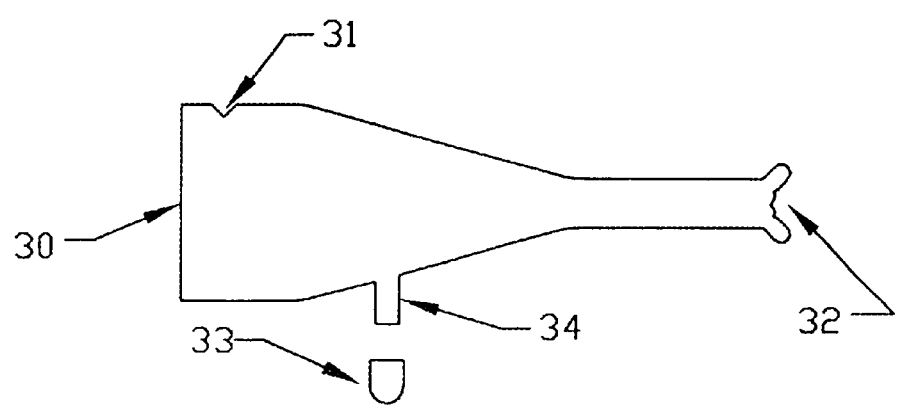
FIG 1    FIG 2    FIG 3

KIT FOR ENHANCED USE OF AN OTOSCOPE

This is a continuation-in-part of Ser. No. 09/517,119 filed Mar. 7, 2000 (pending) which is a continuation-in-part of Ser. No. 09/398,287 filed Sep. 20, 1999, now U.S. Pat No. 6,165,125 which in turn is a continuation-in-part of Ser. No. 09/306,210, filed May 6, 1999 now U.S. Pat. No. 6,001,059 which in turn is a continuation-in-part of Ser. No. 09/080, 894, now U.S. Pat. No. 5,938,590, entitled "An otoscope retrofit to allow multipurpose use" filed May 18, 1998 by inventor P.C. Elliott.

BACKGROUND OF THE INVENTION

An otoscope is an instrument normally designed to allow a physician to peer inside an ear or into a nose through a lighted pathway. At times particularly in infants, there are foreign bodies such as a bead or a bug within an ear or a nose that necessitate removal and at times there is bleeding within a nose that requires cauterizing. This continuation-in-part covers an improved otoscope addition for varying the internal pressure in the otoscope and also covers a basic three part kit with some differing parts to allow a user to simply and rapidly assemble the otoscope retrofit to suit his particular use.

SUMMARY OF THE INVENTION

The invention comprises retrofit pieces to enhance the use of an otoscope comprising an extension piece for the speculum holder, four differing trigger and hinge body pieces that twistably connect with the extension piece, two special trigger body pieces that may connect directly to the speculum and multiple different extension pieces that removably fit into openings in the distal end of the hinge body pieces. A fitting to allow finger pressure variation in the otoscope interior and in a closed extension and a device to allow foot pressure variation in one extension piece is also available. This otoscope kit enhances the utility of the otoscope for both the inspection of a nose and an ear and also enhances the utility for removal of foreign bodies from either a nose or an ear.

BRIEF DESCRIPTION OF THE DRAWINGS

FIG. 1 shows an assembly of one embodiment of the kit

FIG. 2 shows the unit for finger pressure variation

FIG. 3 shows one of the kit extensions

DETAILED DESCRIPTION OF THE INVENTION

Figures 4, 4A:
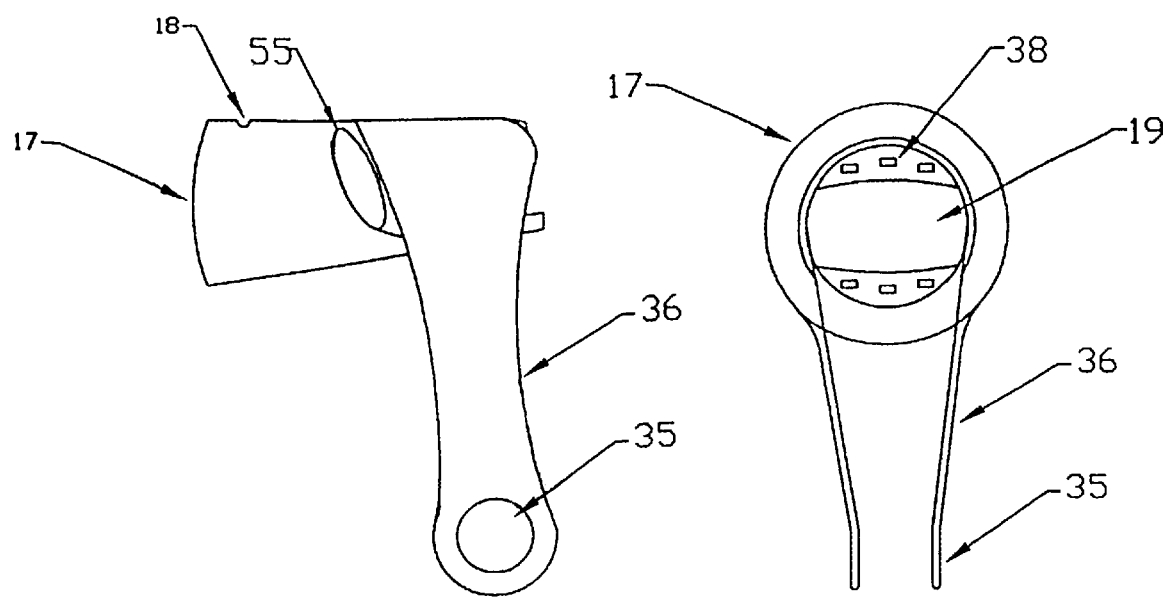
FIG. 4 shows a side view of the trigger piece of the kit
FIG. 4A shows a front view of the trigger piece

The best way to describe the invention is from the drawings. FIG. 1 shows one embodiment of the kit as it would be assembled on the otoscope 1. There are several different units in the kit as outlined herein. Shown installed in FIG. 1 is a pressure-vacuum bulb 3 that used with finger ring 5 can vary the pressure in the otoscope (this unit is shown in detail in FIG. 2). A connector piece 9 with internal projection 13 twistably connects with speculum holder 7 as internal projection 13 twists into slot 12 on the speculum holder 7. A clear plastic closure 11 removably fits in a distal end of connector 9 and may be used when the otoscope head is not used to transmit pressure variation. When flared extension 30 is used and plastic closure 11 is removed and sidearm 34, FIG. 3 is capped pressure-vacuum bulb 3, FIG. 4 may be used to vary the pressure and to pull a vacuum at the flared end 32 to hold an object against end 32. With plastic enclosure 11 in place foot pressure control unit 51, FIG. 6 may be used to pull a vacuum at flared end 32 of extension 30.

Figure 6:
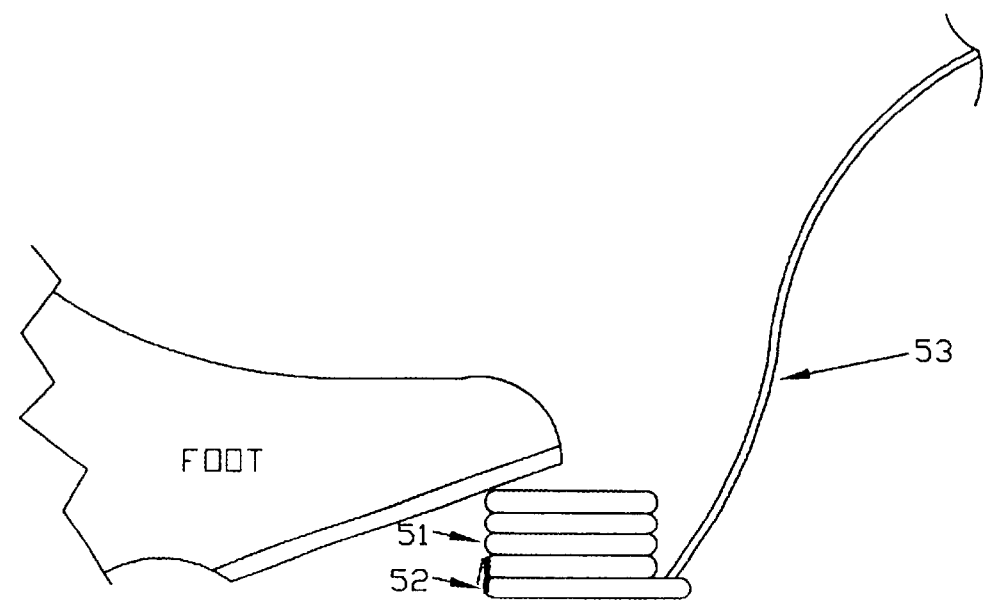
FIG. 6 shows a unit for foot pressure variation of pressure in one extension of the trigger piece

Trigger and hinge body 17 twistably connects with the distal end of connector 9 when internal projection 18 twists into slot 15 in connector 9. The trigger and hinge body 17 is described in more detail in FIG. 4 and FIG. 4A. Ring 21 is used to open and with hinged opening 19 can open and close the distal end of body 17. Projections 40 of extensions 41 fit closely but removably in openings (shown in FIG. 4A) in the distal end of trigger and hinge body 17. FIG. 6 shows a group of extensions similar to 41 that may be included in the kit.

FIG. 2 shows pressure-vacuum bulb 3 that is about one and one half inches long and about one inch in diameter. Open tube type projection 4 fits closely into an opening called the insufflation port in the otoscope and when installed may be used to vary the internal pressure in the otoscope using finger ring 5.

FIG. 3 shows a flared extension 30 that with internal projection 31 twistably connects with connector 9 with projection 31 sliding into slot 15 in connector 9. Sidearm 34 is capped 33 for use with finger pressure variation of internal pressure using pressure-vacuum bulb 3, FIG. 1. and for that use the glass or plastic closure 11 would be removed before connecting the flared extension 30 with connector 9, FIG. 1. Foot pressure variation using a tubing connection to sidearm 34 will be discussed under FIG. 6.

FIG. 4 shows a side view of the trigger and hinge body 17 with dual trigger arms 36 pushed forward using finger ring 35. The shape of opening 19 changes with opening and closing movement of the integrally formed trigger arms 36. At point 55 the hinge body 17 is relatively thin and easily bendable and with relatively thick front portion 38 shown in FIG. 4A slight movement of trigger arms 36 will open or close tip extensions in FIG. 5 when these extensions are fitted into front portion 38 shown in FIG. 4A.

FIG. 4A shows a front view of the trigger and hinge body 17 with three openings shown in the upper part of the trigger body and three openings also shown in the lower part of the trigger body. The base projections of the various tip extensions shown in FIG. 5 fit tightly but removably in any of these openings. The front view of the dual trigger arms 36 and the dual finger rings 35 is also shown.

Figure 5:
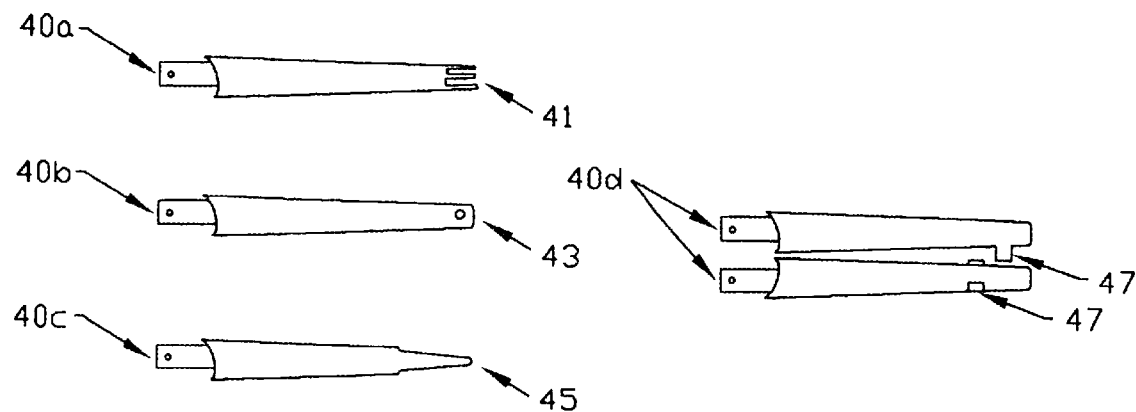
FIG. 5 shows a group of trigger piece extensions

FIG. 5 shows extensions a, b, c, and d all which have projections 40 to attach to the trigger and hinge body by fitting into openings 38, FIG. 4A. Extensions a, b, and c may be used in pairs or for use in looking in a nose would frequently be used with a pair on one side and a single one on the other side of the trigger and hinge body. Extension d with closure guides 47 is shown to indicate that similar extensions would be within the purview of the invention.

FIG. 6 shows a foot compressable corrugated plastic unit 51 made to spring open but compressable to eject air through flapper valve 52 and pull vacuum through the plastic tube 53. With the tube 53 connected with sidearm 34, FIG. 2 and with plate 11, FIG. 1 in place the flared attachment 30, FIG. 2 may be twistably connected with connector 9, FIG. 1 and the flared attachment 30 could then be used with the otoscope with foot pressure to hold an object or material against flared tip 32.

Figure 7:
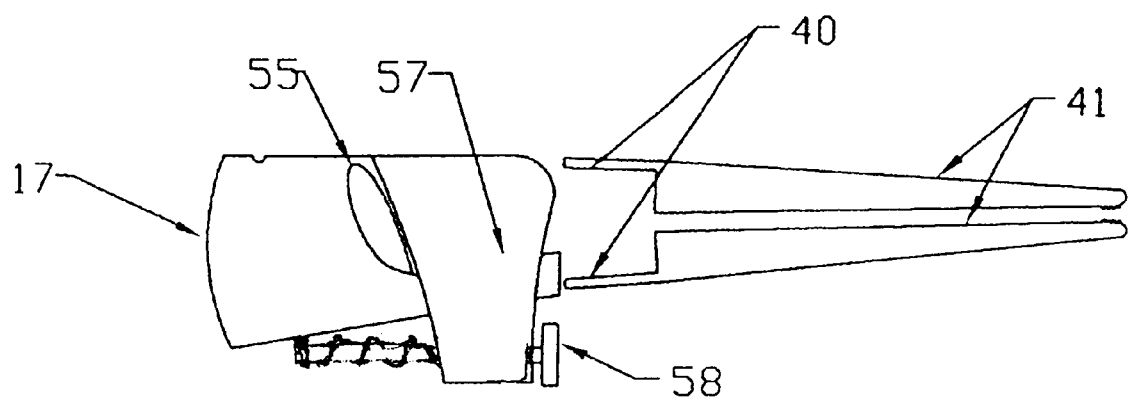
FIG. 7 shows a locking type trigger piece with dual extensions

FIG. 7 shows a trigger and hinge body 55 wherein the two extensions 41 after installing using projections 40 may be manipulated and held in place using the threaded finger wheel 58 on hinge 56. The elongated threads as shown allow adjustment of extensions 41 with minimal movement of finger wheel 58. A pair of extensions 41 are shown before installation to indicate extension placement.

Figure 8:
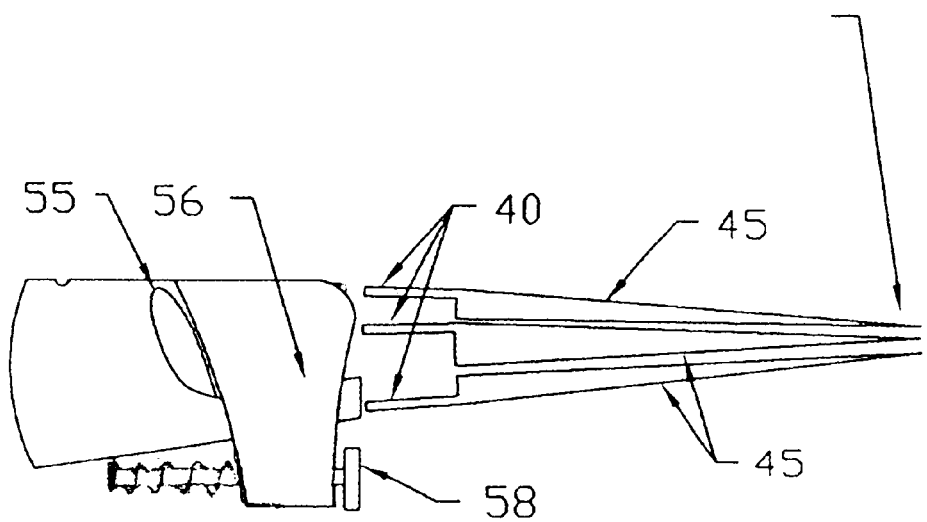
FIG. 8 shows the locking type trigger piece with triple extensions

FIG. 8 shows the same trigger and hinge body 55 as in FIG. 7 but with two extensions 45 on a lower side and one extension 45 on the upper side of said hinged body. This three part extension is frequently used to examine a nose. The extensions are installed with projections 40 forced into openings on the front of the hinged body. Finger wheel 58 with elongated threads allows minimum adjustment of finger wheel 58 to move the single extension tip against tips of the dual extensions.

Figure 9:
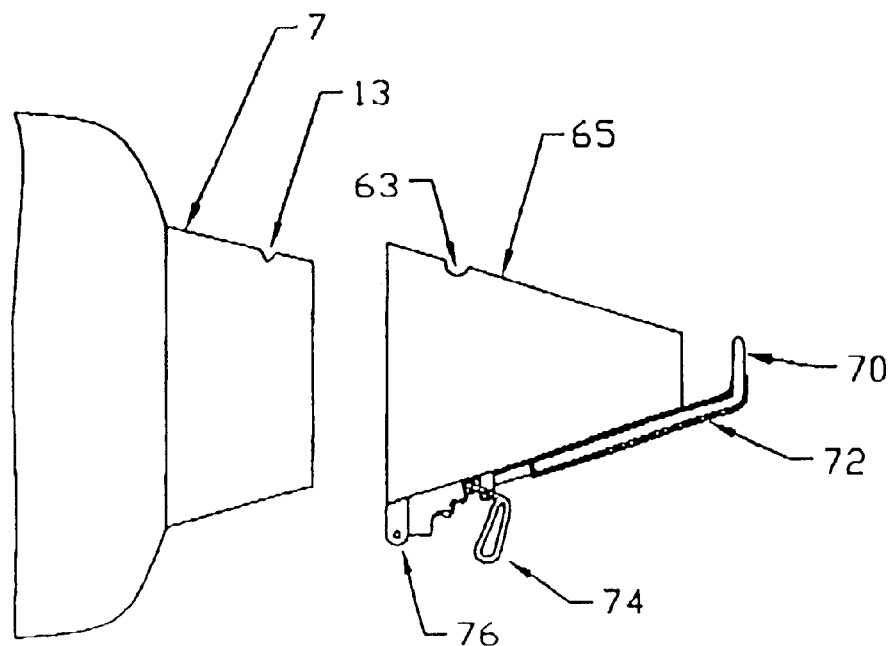
FIG. 9 shows a special trigger body with a fixed extension for use of a wire loop for removal of foreign material or foreign bodies.

FIG. 9 shows a first specialized body or connector piece 65 that twistably connects to the otoscope speculum 7 holder with projection 63 twistably fitting into slot 13 on the speculum holder 7. Wire guide 72 is fastened to the lower side of the cone shaped body 65 and has a U shaped opening on anterior end with a beginning end of wire 70 fastened to one side of the U shaped opening with the other end of wire 70 fastened above the pivot point of trigger 74 so that pulling back on trigger 74 forms a loop as shown. Releasing trigger 74 allows retractor spring 76 to pull wire 70 back into the wire guide 72. Thus the user may form a loop in back of foreign material or a foreign object to aid in removal thereof.

Figure 10:
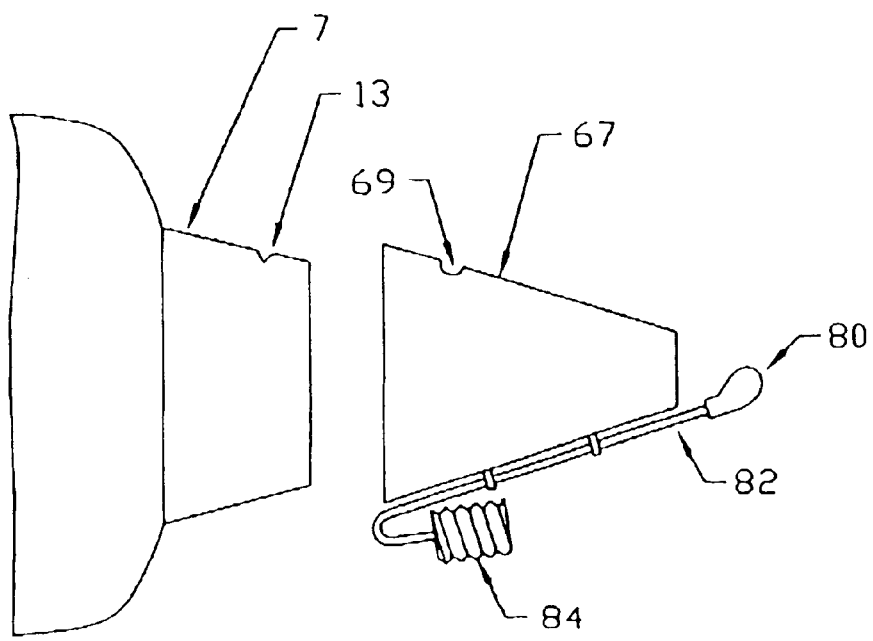
FIG. 10 shows a second special trigger body with a fixed extension to form a balloon behind a foreign body or foreign material in the ear.

FIG. 10 is a second specialized body 67 that twistably attaches to the otoscope speculum holder 7 with interior ridge 69 twisting into slot 13 in the speculum holder 7. Balloon air pipe 82 is glued or otherwise fastened to body 65 and has an anterior end covered with an expandable plastic material and has the anterior end so shaped as to form a balloon when finger compressible unit 84 is compressed. Thus a user may form a balloon behind a foreign object in an ear or nose and aid in the removal of the foreign object.

What is claimed is:

1. A kit for enhanced use of an otoscope comprising:
    a) a first connector piece to twistably connect to the a speculum holder on said Otoscope;
    b) a first type twist on trigger connector piece with a pull-push trigger pull integrally formed therein to twistably connect to a distal end of said first connector piece; both upper and lower distal ends of said trigger connector piece having openings therein;
    c) a group of extensions, each having a basal projection to fit firmly but removably into said openings in said distal ends of said trigger connector piece and each having small distal ends to aid in removing foreign material from an ear and nose;
    d) a clear plastic closure plate to removably seal a distal end of said first connector piece;
    e) a twist on flared extension piece with a cappable side connection to connect to a distal end of said first connector piece.

2. A kit for enhanced use of an otoscope as in claim 1 further comprising a second type trigger connector piece with a locking type trigger therein to twistably connect with a distal end of said first connector piece.

3. A kit for enhanced use of an otoscope as in claim 2 wherein two extensions are used in a first distal end and one extension is used in a second distal end of said trigger connector piece to allow holding a nose open for inspection and/or removal of a foreign body.

4. A kit for enhanced use of an otoscope as in claim 1 further comprising a foot operated compressible unit with a flexible hose connection to connect to said cappable side connection of said flared extension.

5. A kit for enhanced use of an otoscope as in claim 1 wherein two extensions are used in a first distal end and one extension is used in a second distal end of said trigger connector piece to allow holding a nose open for inspection and/or removal of a foreign body.

6. A kit for enhanced use of an otoscope as in claim 1 further comprising a first specialized cone shaped connector piece to twistably connect with said speculum holder, said specialized cone shaped connector piece having a cylindrical wire guide, and means whereby finger pressure on a trigger may push forward a spring loaded wire in said wire guide to form a wire loop at near right angles to said wire guide thereby allowing a user while looking within an ear to form said wire loop behind foreign material and thereby facilitate removal thereof.

7. A kit for enhanced use of an otoscope as in claim 1 further comprising a second specialized cone shaped connector piece to twistably connect with said speculum holder; said second specialized cone shaped connector piece having an air filled tube connected to an underside and extending in front of a cone shaped connected body with a beginning end of said tube covered with an expandable plastic and so shaped that finger pressure on a compressible unit in a rearward end of said tube allows a user while looking within an ear to form a balloon in back of foreign material and aid in removal thereof.

8. A kit for enhanced use of an otoscope comprising:
    a) a first connector piece to twistably connect to a speculum holder on said Otoscope;
    b) a first type twist on trigger connector piece with a pull-push trigger pull integrally formed therein to twistably connect to a distal end of said first connector piece; both upper and lower distal ends of said trigger connector piece having openings therein;
    c) a group of extensions, each having a basal projection to fit firmly but removably into said openings in said distal ends of said trigger connector piece and each having small distal ends to aid in removing foreign material from an ear and nose.

9. A kit for enhanced use of an otoscope as in claim 8 further comprising a first specialized cone shaped connector piece to twistably connect with said speculum holder, said specialized cone shaped connector piece having a cylindrical wire guide, and means whereby finger pressure on a trigger may push forward a spring loaded wire in said wire guide to form a wire loop at nearly right angles to said wire guide thereby allowing a user while looking within a nose to form said wire loop behind foreign material and thereby facilitate removal thereof.

10. A kit for enhanced use of an otoscope as in claim 8 further comprising a second specialized cone shaped connector to twistably connect with said speculum holder; said second specialized cone shaped connector piece having an air filled tube connected to an underside and extending in front of said cone shaped connector body with a beginning end of said tube covered with an expandable plastic and so shaped that finger pressure on a compressible unit in a rearward end of said tube allows a user while looking within a nose to form a balloon in back of foreign material and aid in removal thereof.

* * * * *